United States Patent [19]

Sach

[11] Patent Number: 4,486,434

[45] Date of Patent: Dec. 4, 1984

[54] HISTAMINE H$_1$-ANTAGONISTS

[75] Inventor: George S. Sach, Welwyn, England

[73] Assignee: Smith Kline & French Laboratories Limited, Welwyn Garden City, England

[21] Appl. No.: 391,076

[22] Filed: Jun. 22, 1982

[30] Foreign Application Priority Data

Jun. 27, 1981 [GB] United Kingdom .................. 8119906

[51] Int. Cl.$^3$ .................. C07D 401/14; A61K 31/505
[52] U.S. Cl. ..................................... 424/251; 544/320
[58] Field of Search ......................... 544/320; 424/251

[56] References Cited

U.S. PATENT DOCUMENTS

| 4,154,834 | 5/1979 | Brown et al. | 424/251 |
| 4,216,318 | 8/1980 | Brown et al. | 544/310 |
| 4,255,428 | 3/1981 | Brown et al. | 424/251 |

Primary Examiner—Robert Gerstl
Attorney, Agent, or Firm—Joan S. Keps; Richard D. Foggio; Alan D. Lourie

[57] ABSTRACT

The invention provides 2-(3,5-disubstituted pyridylalkyl amino)-5-pyridylmethyl-4-pyrimidone derivatives which are useful as histamine H$_1$-antagonists.

12 Claims, No Drawings

HISTAMINE H₁-ANTAGONISTS

This invention relates to certain pyrimidone derivatives, compositions containing them and a method of blocking histamine H$_1$-receptors by administering them.

Histamine, a physiologically active compound endogenous in mammals, exerts its action by interacting with certain sites called receptors. One type of receptor is known as a histamine H$_1$-receptor (Ash and Schild, Brit. J. Pharmac. 1966, 27, 427) and the actions of histamine at these receptors are inhibited by drugs commonly called "antihistamines" (histamine H$_1$-antagonists) a common example of which is mepyramine. A second type of histamine receptor is known as the H$_2$-receptor (Black et al Nature 1972, 236, 385). The actions of histamine at these receptors are not inhibited by mepyramine but are inhibited by burimamide. Compounds which inhibit the actions of histamine at histamine H$_2$-receptors are called histamine H$_2$-antagonists.

U.S. Pat. No. 4,154,834 discloses compounds of general formula (1):

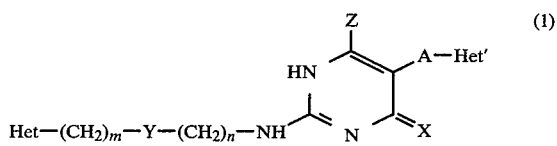

where Het is 2- or 4-imidazolyl optionally substituted by lower alkyl (preferably methyl), halogen (preferably chlorine or bromine), trifluoromethyl or hydroxymethyl; 2-pyridyl optionally substituted by one or two groups (which may be the same or different) selected from lower alkyl (preferably methyl), lower alkoxy (preferably methoxy), halogen (preferably chlorine or bromine), amino and hydroxy; 2-pyridyl with a phenyl, carbocyclic or cyclic ether ring containing 2 oxygen atoms fused to it; 2-thiazolyl; 3-isothiazolyl optionally substituted by chlorine or bromine; 3-(1,2,5)-thiadiazolyl optionally substituted by chlorine or bromine, or 2-(5-amino-1,3,4-thiadiazolyl); Y is sulphur or a methylene group; m is 0, 1 or 2 and n is 2 or 3 such that their sum is 3 or 4 or when Y is methylene and Het is other than an imidazole ring, 2; Z is hydrogen or lower alkyl (preferably methyl); X is oxygen or sulphur; A is a straight or branched alkylene chain containing from 1–5 carbon atoms or —(CH$_2$)$_p$W(CH$_2$)$_q$— where W is oxygen or sulphur and p and q are such that their sum is from 1 to 4; Het' is a 5 or 6 membered heterocyclic ring selected from pyridine, pyridine-N-oxide, furan, thiophen, thiazole, oxazole, isothiazole, imidazole, pyrimidine, pyrazine, pyridazine or thiadiazole, which ring is optionally substituted by one or two (which may be the same or different) of the groups selected from lower alkyl, lower alkoxy, halo, hydroxy and amino, or Het' is a pyridine ring with a carbocyclic or cyclic ether ring containing two oxygen atoms fused to it, or Het' is a pyridine, imidazole or thiazole ring which has a benzene ring fused to it; and pharmaceutically acceptable salts thereof. These compounds are described as having combined histamine H$_1$- and H$_2$-antagonist activity.

In particular U.S. Pat. No. 4,154,834 discloses compounds of formula (1) where Het is 2-pyridyl having a substitutent in position 3, Y is methylene and Het' is substituted pyridyl. It has now been found that when the 2-pyridyl group Het has a second substituent in position 5 the relative level of H$_1$ to H$_2$ activity increases. A small number of compounds, which fall within the general class of compounds of formula (1), have now been found to be useful as histamine H$_1$-antagonists, that is, for the treatment of diseases for example bronchial asthma, rhinitis, hayfever and allergic eczema whose symptoms are mediated through the action of histamine at H$_1$-receptors.

Accordingly the present invention provides compounds of formula (2):

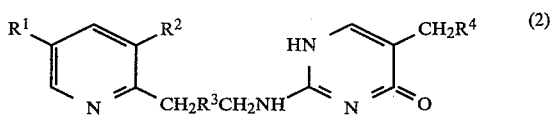

and pharmaceutically acceptable salts thereof; where R$^1$ is halogen or nitro; R$^2$ is C$_{1-4}$ alkyl; R$^3$ is a C$_{1-3}$ alkylene group; and R$^4$ is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

R$^1$ can represent any one of the halogens, fluorine, chlorine, bromine or iodine.

Preferably R$^1$ is bromine.

Examples of C$_{1-4}$ alkyl groups for R$^2$ are methyl, ethyl, n-propyl, iso-propyl, n-butyl and t-butyl.

Preferably R$^2$ is methyl.

By way of example —R$^3$— can be methylene, 1,2-ethanediyl, or 1,3-propanediyl.

Preferably R$^3$ is 1,2-ethanediyl or 1,3-propanediyl.

Preferably the group R$^4$ is an optionally substituted 3-pyridyl group. Preferably one substituent occupies position 6. Thus R$^4$ is preferably 6-methylpyrid-3-yl.

Examples of compounds within the scope of this invention are:

2-[4-(5-nitro-3-methylpyrid-2-yl)butylamino]-5-(6-methylpyrid-3-ylmethyl)-4-pyrimidone;

2-[4-(5-chloro-3-methylpyrid-2-yl)butylamino]-5-(6-methylpyrid-3-ylmethyl)-4-pyrimidone;

2-[4-(5-iodo-3-methylpyrid-2-yl)butylamino]-5-(6-methylpyrid-3-ylmethyl)-4-pyrimidone;

2-[4-(5-fluoro-3-methylpyrid-2-yl)butylamino]-5-(6-methylpyrid-3-ylmethyl)-4-pyrimidone;

and their pharmaceutically acceptable salts.

Examples of compounds within the scope of this invention having the preferred R$^1$ and R$^2$ substituents are:

2-[4-(5-bromo-3-methylpyrid-2-yl)butylamino]-5-(6-methylpyrid-3-ylmethyl)-4-pyrimidone;

2-[4-(5-bromo-3-methylpyrid-2-yl)butylamino]-5-(pyrid-4-ylmethyl)-4-pyrimidone;

2-[4-(5-bromo-3-methylpyrid-2-yl)butylamino]-5-(6-hydroxymethylpyrid-3-ylmethyl)-4-pyrimidone;

and their pharmaceutically acceptable salts.

2-[4-(5-Bromo-3-methylpyrid-2-yl)butylamino]-5-(6-methylpyrid-3-ylmethyl)-4-pyrimidone has been shown to have the particular advantage that it does not enter the central nervous system. This has been shown by rat whole body radiography.

The compounds of formula (2) are shown and described as 4-pyrimidones which exist in equilibrium with the corresponding 6-one tautomers. These compounds also exist to a lesser extent as the hydroxy tautomers, and the pyrimidine ring may also exist in the following tautomeric forms:

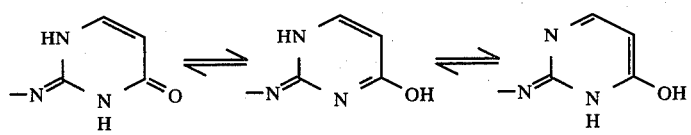

It will be understood that all these tautomeric forms are within the scope of the present invention.

The compounds of formula (2) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

The compounds of this invention can be made by a process which comprises reacting a compound of formula (3):

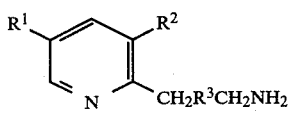

or a salt thereof, where $R^1$, $R^2$ and $R^3$ are as defined with reference to formula (2) with a compound of formula (4):

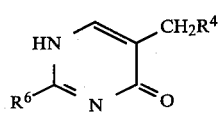

where $R^4$ is as defined with reference to formula (2) and $R^6$ is a group displaceable with amine, thereafter where $R^4$ is N-oxo-6-methyl-3-pyridyl; N-oxo-4,6-dimethyl-3-pyridyl; or N-oxo-5,6-dimethyl-3-pyridyl; converting the compound of formula (2) so obtained into the corresponding compound of formula (2) where $R^4$ is 6-hydroxymethyl-3-pyridyl; 6-hydroxymethyl-4-methyl-3-pyridyl; or 6-hydroxymethyl-5-methyl-3-pyridyl; and optionally converting the compound of formula (2) so obtained into a pharmaceutically acceptable salt.

The compounds of formula (2) where $R^4$ is N-oxo-6-methyl-3-pyridyl; N-oxo-4,6-dimethyl-3-pyridyl; or N-oxo-5,6-dimethyl-3-pyridyl can be converted into the corresponding compound of formula (2) where $R^4$ is 6-hydroxymethyl-3-pyridyl; 6-hydroxymethyl-4-methyl-3-pyridyl; or 6-hydroxymethyl-5-methyl-3-pyridyl; by reacting with an organic anhydride for example trifluoroacetic anhydride.

Pharmaceutically acceptable salts of compounds of formula (2) can be prepared by standard methods, for example by reacting a solution of the compound of formula (2) with a solution of the acid.

Examples of groups $R^6$ are $C_{1-4}$ alkylthio (particularly methylthio), benzylthio, chlorine, bromine and nitroamino. Preferably $R^6$ is nitroamino.

The reaction can be carried out at an elevated temperature in the absence of a solvent, for example at from 80° to 170° C., preferably from 120° to 140°, or in a solvent at an elevated temperature, for example at the reflux temperature of the reaction mixture. The choice of solvent is affected by solubility characteristics of the reactants and the nature of $R^6$. Preferably the solvent is pyridine, a picoline or mixture of picolines, a $C_{1-4}$ alkanol, preferably ethanol or 1-propanol, a $C_{1-4}$ alkanol, 1,2-ethanediol, a ketone, for example acetone or 2-butanone, a high boiling alkoxyaryl ether for example anisole, or a polar aprotic solvent, for example dimethylformamide, dimethylacetamide, dimethylsulphoxide, hexamethylphosphoramide, sulpholane, acetonitrile or nitromethane.

Compounds of formula (3) can be prepared by carrying out a Sandmeyer reaction on the corresponding compound of formula (3a):

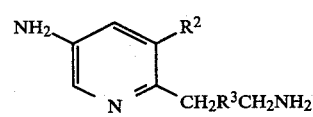

that is by diazoatisation of the amino group $R^1$ and displacing the diazo group with halo.

Compounds of formula (3) can also be prepared by halogenating the corresponding compound of formula (3b):

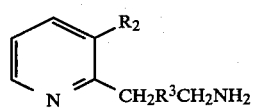

where $R^2$ and $R^3$ are as defined with reference to formula (2) with halogen.

The amines of formula (3) where $R^1$ is bromine may be prepared as follows:

Thus a compound of formula (3c):

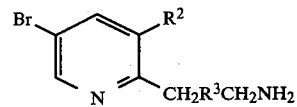

and salts thereof where $R^2$ and $R^3$ are as defined with reference to formula (2) can be prepared by reacting a compound of formula (3b):

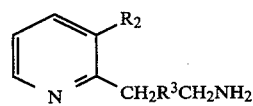

or a salt thereof, where $R^2$ and $R^3$ are as defined with reference to formula (2), with an electrophilic brominating agent.

Examples of electrophilic brominating agents are bromine or dibromocyanuric acid in a polar medium which generates $Br^+$. Examples of such media are oleum and fluorosulphonic acid. $Br^+$ can also be generated from hydrobromic acid and bromide ion in oxidizing or oxidizing polar media. For example hydrobromic acid is oxidized by solutions of sulphur trioxide to bromine which dissociates giving Br+. The sulphur trioxide solution can be in a freon for example 1,1,2-trifluorotrichloroethane or in sulphuric acid i.e. oleum. The hydrobromic acid can be derived from the dihydrobromide salt of the compound of formula (3b), particularly when the reaction is carried out using sulphur trioxide and freon. Where the sulphur trioxide solution is oleum, the hydrobromic acid can be generated from a bromide salt for example an alkali metal salt in particular potassium bromide.

Compounds of formula (3b) form neutral complexes with sulphur trioxide. The effect of this is that the pyridine ring in the compounds of formula (3b) is activated to bromination. Thus preferably the medium is one which dissolves sulphur trioxide.

Two preferable media for carrying out the bromination reactions are oleum and sulphur trioxide in freon. Where the medium is oleum, in practice it is at least 20% w/w. Preferably it is at least 65% w/w. The more concentrated the oleum, the lower is the temperature at which the reaction can be carried out. For example where the medium is 20% oleum the reaction requires elevated temperatures to proceed in a short period and at this concentration of oleum it is carried out at 100° C. and above. Where the medium is 65% oleum the reaction can be carried at from 0° C. to 100° C., preferably from 50°–60° C. especially 55°–58° C.

Where the medium is sulphur trioxide in freon the reaction is carried out at from ambient temperature to the reflux temperature of the solvent.

Compounds of formula (3) and (3a) can also be prepared by reducing a corresponding cyano compound of formula (5):

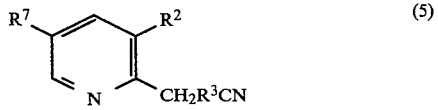

where $R^7$ is halogen, nitro or amino and $R^2$ and $R^3$ are as defined with reference to formula (2) with a reducing agent which reduces cyano to amino without reducing the group $R^7$ in a reaction medium which is inert to the reagents and product. For example the reducing agent can be lithium aluminium hydride or diborane. The reaction medium can be a dialkyl ether for example diethyl ether or a cyclic ether for example tetrahydrofuran or dioxan. Where the reducing agent is lithium aluminium hydride or diborane it will be appreciated that the reaction medium is anhydrous.

Compounds of formula (5) where $R^7$ is amino can also be prepared by reducing the corresponding nitro-compound of formula (5) where $R^7$ is nitro. The reduction can be carried out by hydrogenation.

Compounds of formula (5) can be prepared by reacting a disubstituted chloropyridine of formula (6):

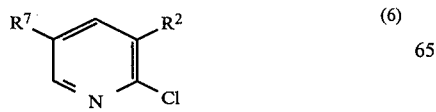

where $R^2$ is as defined with reference to formula (2) and $R^7$ is halogen, nitro or amino; with a malonic acid ester of formula (7):

where $R^3$ is as previously defined and R is an ester forming group, in the presence of a strong base in an inert reaction medium, and thereafter de-esterifying and decarboxylating the product.

In particular the groups R can be ethyl.

In particular the strong base can be sodium hydride.

The reaction medium is one which is substantially inert to the reagents and product. In particular the medium can be dry tetrahydrofuran.

Compounds of formula (3b) can also be prepared by reacting an alkali metal derivative of a compound of formula (8):

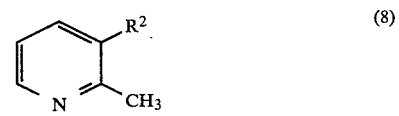

where $R^2$ is as defined with reference to formula (2) with a compound of formula (9):

$$XR^3NH_2 \qquad (9)$$

or a salt thereof where X is halogen and $R^3$ is as defined with reference to formula (2).

In the compound of formula (9), X can be chlorine, bromine or iodine. In particular it is chlorine.

The alkali metal derivative can be a lithium, sodium or potassium derivative. In particular it is the sodium derivative.

The alkali metal derivative of compound of formula (8) can be prepared in situ by reacting the compound of formula (8), with an alkali metal amide (in particular sodamide, where the alkali metal is sodium) in which case the solvent is preferably liquid ammonia or an alkyl alkali metal (in particular butyl lithium, where the alkali metal is lithium) in which case the solvent is preferably an ether, for example diethylether or tetrahydrofuran.

This reaction is carried out at reduced temperatures. For example where the reaction is carried out in liquid ammonia, the temperature is at or below the boiling point of ammonia and where a derivative of formula (8) is generated in situ from an alkyl alkali metal the reaction is carried out at liquid nitrogen temperature, preferably in an inert atmosphere.

The compounds of formula (8) and (9) are known or can be made by known methods.

The compounds of formula (4):

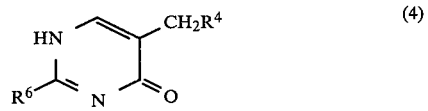

are known or can be made by analogy with known processes as disclosed in for example U.S. Pat. No.

4,154,834 and European Patent Specification No. 17,679.

Compounds of formula (2) can also be prepared by reacting a guanidine of formula (10):

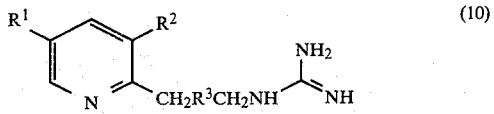

where $R^1$, $R^2$ and $R^3$ are as defined with reference to formula (2) with a compound of formula (11):

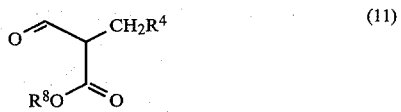

where $R^4$ is as defined with reference to formula (4) and $R^8$ is $C_{1-4}$ alkyl (particularly ethyl) benzyl or phenyl.

The reaction can be carried out by heating the guanidine of formula (10) with the compound of formula (11) optionally in a solvent for example an alcohol corresponding to the ester function in the compound of formula (11) that is $R^8OH$, at an elevated temperature, preferably in the presence of a base in particular the sodium alkoxide $NaOR^8$ corresponding to the ester function of the compound of formula (11).

The guanidines of formula (10) can be prepared by reacting an amine of formula (3) with a compound of formula (12):

where $R^9$ is a leaving group for example methylthio or 3,5-dimethylpyrazolyl.

The histamine $H_1$-antagonist activity of the compounds of formula (2) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity ($pA_2$ value). The compounds of Examples 1 to 12 have $pA_2$ values greater than 8.

The histamine $H_2$-antagonist activity of the compounds of formula (2) can be demonstrated in vitro in the guinea pig atrium test. In this test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity ($pA_2$ value). The compounds of Examples 1 to 12 have $pA_2$ values of less than 7.5.

The activity of compounds of formula (2) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist. The compounds of the Examples hereafter cause displacement of histamine dose-response curves with a dose-ratio of 10 at doses of less than 0.8 micromole $kg^{-1}$ i.v.

The activity of the compounds of formula (2) as histamine $H_2$-antagonists can be demonstrated in vivo by the inhibition of histamine-stimulated secretion of gastric acid from the lumen-perfused stomachs of rats anaesthetised with urethane. This procedure is referred to in Ash and Schild, Brit. J. Pharmac. Chemother., 27, 247 (1966). The compounds of the Examples hereafter cause 50% inhibition of maximal acid secretion at doses of 0.1 to 30 micromole $kg^{-1}$ i.v.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (2) or a pharmaceutically acceptable salt thereof and a pharmaceutically acceptable carrier.

Compounds of formula (2) and their pharmaceutically acceptable salts can be administered topically or systemically.

Topical formulations for administration of the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (2) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (2) or a pharmaceutically acceptable salt thereof calculated as the free base.

The invention also provides a method of blocking histamine $H_1$-receptors which comprises administering to a subject an effective amount to block said receptors of a compound of formula (2) or a pharmaceutically acceptable salt thereof.

The compounds of formula (2) and their pharmaceutically acceptable salts will normally be administered to a subject for the treatment of rhinitis, hayfever, bronchial asthma or allergic eczema in pharmceutical compositions as described above. An adult subject will receive an oral dose of between 15 mg and 400 mg and preferably between 15 mg and 200 mg or an intravenous, subcutaneous or intramuscular dose of between 1 mg and 50 mg, and preferably between 1 mg and 10 mg of compound of formula (I) or pharmaceutically acceptable salt thereof calculated as the free base, the composition being administered 1 to 4 times per day.

The following Examples illustrate the invention.

EXAMPLES

Example 1

(a) 2-(2-Cyanoethyl)malonic acid diethyl ester (148.3 g) was reacted with sodium hydride (15.3 g) in tetrahydrofuran at 20° C. 2-Chloro-3-methyl-5-nitropyridine (100 g) was added and the internal temperature was raised to 100° C. (some tetrahydrofuran was distilled off) over 14 hrs. The reaction mixture was partitioned between water and chloroform, the chloroform extract was dried, treated with charcoal and filtered through a silica bed and then evaporated to dryness. Crystallisation of the residue from ethanol gave 4-(3-methyl-5-nitropyrid-2-yl)-4,4-bis(carbethoxy)-butyronitrile (99 g) m.p. 64°–65.5° C.

(b) 4-(3-Methyl-5-nitropyrid-2-yl)-4,4-bis(carbethoxy)butyronitrile (99 g) was stirred in a mixture of ethanol (1200 ml) and sodium hydroxide solution (1130 ml, molar) for 16 hours. The pH was lowered to 2 by the addition of hydrochloric acid, and the ethanol was distilled off. The product was extracted with chloroform to leave an oil (57.1 g). This oil was extracted with dilute hydrochloric acid (554 ml; 1.5N), re-extracted with more dilute hydrochloric acid and the combined acid extracts were treated with charcoal, filtered and then extracted with chloroform, to give 5-nitro-2-(3-cyanopropyl)-3-methylpyridine (49.5 g) m.p. 51.5°–53° C.

(c) 5-Nitro-2-(3-cyanopropyl)-3-methylpyridine (5.9 g) was hydrogenated in ethanol (150 ml) with palladium on charcoal (0.59 g of 10%) at 140 kPa, for 2.5 hrs. The filtered solution was concentrated to dryness, the residue was triturated with ether to give 5-amino-2-(3-cyanopropyl)-3-methylpyridine (4.70 g) m.p. 103°–105° C.

(d) 5-Amino-2-(3-cyanopropyl)-3-methylpyridine (23.0 g) was reduced with lithium aluminium hydride (12.47 g) in a mixture of tetrahydrofuran (750 ml) and diethylether (750 ml) over 3 hours, to give 5-amino-2-(4-aminobutyl)-3-methylpyridine (20.8 g) as an amber oil. N.M.R. (CDCl$_3$): assignment, $\delta$ (p.p.m.) multiplicity; —$CH_2$ $CH_2$ $CH_2$ $NH_2$, 1.3–1.9, m; 3—$CH_3$, 2.22, s; $CH_2(CH_2)_2CH_2NH_2$, 2.6–2.8, m; 5—$NH_2$, ca 3.5, broad resonance; 4-pyridyl proton, 6.77, d; 6-pyridyl proton, 7.88, d.

(e) 5-Amino-2-(4-aminobutyl)-3-methylpyridine (5.11 g) in hydrobromic acid (48%, 47 ml) was reacted with cuprous bromide (4.98 g) and copper bronze (0.18 g). A solution of sodium nitrite (2.45 g) in water (16 ml) was added at 5° to 8° C. over 45 minutes, the reaction mixture was allowed to stir at 5° to 8° C. for a further hour and then stirred at room temperature for 3.5 hours. The reaction mixture was diluted with water, and hydrogen sulphide gas was passed, while the pH was progressively raised to 11 by the addition of sodium hydroxide solution. The precipitated copper salts were filtered off at intervals during the above procedure. The product was then extracted at pH 11 with chloroform to give 5-bromo-2-(4-aminobutyl)-3-methylpyridine (4.95 g) m.p. 35°–37° C.

(f) 5-Bromo-2-(4-aminobutyl)-3-methylpyridine (2.12 g) and 2-nitroamino-5-(6-methylpyrid-3-ylmethyl)-4-pyrimidone (3.18 g) were refluxed in pyridine (12 ml)

for 9.5 hrs. The pyridine was removed in vacuo and the residue was re-evaporated with n-propanol (2×50 ml), triturated with chloroform, filtered and the solution was chromatographed on silica in chloroform-methanol (10:1). The product was crystallised from ethanol-ether to give 2-[4-(5-bromo-3-methylpyrid-2-yl)-butylamino]-5-(6-methylpyrid-3-yl-methyl)-4-pyrimidone (2.44 g) m.p. 151°–152° C.

$C_{21}H_{24}BrN_5O$: Requires: C, 57.01; H, 5.46; N, 15.83; Br, 18.06; Found: C, 56.83; H, 5.30; N, 15.69; Br, 18.11.

Alternatively and preferably 5-bromo-2-(4-aminobutyl)-3-methylpyridine can be prepared by any of the methods of Example 1, parts g to j hereafter.

(g) 2,3-Lutidine (321 g) was added with stirring to a solution of sodamide (351 g) in liquid ammonia (3 l). 1-Amino-3-chloropropane hydrochloride (429 g) was added to this mixture over 8 minutes with stirring. Any liquid ammonia lost through evaporation was replaced. After 2 hours the reaction was quenched by the addition of ammonium chloride (120 g) and the reaction mixture was left to stand overnight to allow substantially complete escape of ammonia through evaporation. The residue so obtained was diluted with water (2 l) and extracted with dichloromethane. The extracts were dried ($Na_2SO_4$), the dichloromethane removed by evaporation and the residue distilled in vacuo to give 2-(4-aminobutyl)-3-methylpyridine (306.6 g).

(h) Bromine (10 g) was added dropwise with stirring to a solution of 2-(4-aminobutyl)-3-methylpyridine sulphate (21.3 g) obtained from 2-(4-aminobutyl)-3-methylpyridine and concentrated sulphuric acid) in 65% oleum (100 ml) at room temperature. The solution was then heated to 55° C. and stirred overnight. The solution was cooled and added slowly to ice (38 g). The resultant solution was poured into water (250 ml) and taken to pH 2.5 with aqueous ammonia solution (s.g. 0.88) and a dibrominated impurity crystallized which was removed by filtration. The filtrate was taken to pH 9.5 and extracted with dichloromethane and the extracts were dried ($MgSO_4$) and decolourised with charcoal.

Acetic anhydride (19 ml) was added to the dried extract and the mixture was heated under reflux for 30 min. After cooling the mixture was washed with water and potassium carbonate solution (56% w/v) which removed any unbrominated starting material. The organic layer was dried ($MgSO_4$) and the solvent evaporated at reduced pressure the residue (18.4 g) heated ca 16 hr. on a steam bath with conc. hydrochloric acid. The solution so obtained was cooled, taken to pH 9.5 with aqueous ammonia solution (s.g. 0.88) and extracted with dichloromethane. The organic phase was dried and the solvent evaporated at reduced pressure to yield 5-bromo-2-(4-aminobutyl)-3-methylpyridine (12.4 g) as a yellow oil which crystallised on being left to stand.

(i) A solution of sulphur trioxide (150 ml) in 1,1,2-trifluorotrichloroethane (350 ml) was added over ca 30 min. to a suspension of 2-(4-aminobutyl)-3-methyl-pyridine dihydrobromide (17 g) [prepared by passing hydrogen bromide gas through a solution of the amine in dichloromethane] in 1,1,2-trifluorotrichloroethane (100 ml) and the mixture was heated under reflux for ca 16 hr. The solvent was removed by distillation and unbrominated starting material was removed by acetylation as described in Example 1(h) to yield 5-bromo-2-(4-aminobutyl)-3-methylpyridine (6.53 g) as an oil.

(j) A solution of sulphur trioxide (150 ml) in 1,1,2-trifluorotrichloroethane (550 ml) was added over 30 min to a suspension of 2-(4-aminobutyl)-3-methylpyridine hydrobromide (14.2 g) [prepared by reacting 2-(4-aminobutyl)-3-methyl-pyridine with hydrobromic acid (0.89M)] in 1,1,2-trifluoro-trichloroethane and to this mixture was added liquid bromine (5.56 g). The mixture was heated under reflux for ca 16 hr. The solvent was removed by distillation and unbrominated starting material was removed by acetylation as described in Example 1(h) to yield 5-bromo-2-(4-amino-butyl)-3-methylpyridine (6.49 g) as an oil.

Example 2

Reacting 5-bromo-2-(4-aminobutyl)-3-methylpyridine, the product from Example 1(e) (0.5 g), with 2-methylthio-5-(pyrid-4-ylmethyl)-4-pyrimidone (0.57 gm) under conditions analogous to those described in Example 1(f) gave 2-[4-(5-bromo-3-methylpyrid-2-yl)-butylamino]-5-(pyrid-4-ylmethyl)pyrimidone (0.15 gm) m.p. 176°–177.5° C.

$C_{20}H_{22}BrN_5O$: Requires: C, 56.08; H, 5.17; N, 16.35; Br, 18.65; Found: C, 56.18; H, 5.08; N, 16.45; Br, 18.43.

Example 3

Reacting 5-bromo-2-(4-aminobutyl)-3-methylpyridine, the product from Example 1(e) (1.04 g), with 2-nitroamino-5-(N-oxo-6-methylpyrid-3-ylmethyl)-4-pyrimidone (1.42 g) under conditions analogous to those described in Example 1(f) gave 2-[4-(5-bromo-3-methylpyrid-2-yl)-butylamino]-5-(N-oxo-6-methylpyrid-3-ylmethyl)-4-pyrimidone (0.48 g) m.p. 193°–194.5° C.

$C_{21}H_{24}BrN_5O_2$: Requires: C, 55.03; H, 5.28; N, 15.28; Br, 17.43; Found: C, 54.67; H, 5.41; N, 15.09; Br, 17.60.

Example 4

2-[4-(5-Bromo-3-methylpyrid-2-yl)butylamino]-5-(N-oxo-6-methylpyrid-3-ylmethyl)-4-pyrimidone (the product of Example 3) (0.9 g) was reacted with trifluoroacetic anhydride (1.65 g) in dichloromethane (6 ml) for two days, followed by removal of the solvent in vacuo, dissolution of the residue in chloroform, washing of the chloroform solution with 10% sodium bicarbonate solution, and concentrating the chloroform solution to dryness gave 2-[4-(5-bromo-3-methylpyrid-2-yl)-butylamino]-5-(6-hydroxymethylpyrid-3-yl-methyl)-4-pyrimidone (0.42 g), m.p. 61°–70° C.—resolidifying ca 120° C., remelts 160°–165° C.

$C_{21}H_{24}BrN_5O_2$, $1.23H_2O$: Requires: C, 52.50; H, 5.50; N, 14.58; Found: C, 52.34; H, 5.35; N, 14.49; (Weight loss 40°–80° C., 4.6%=1.23 $H_2O$).

Example 5

(a) Reaction of 5-amino-2-(4-aminobutyl)-3-methylpyridine (the product of Example 1(d)) (1.5 g), with sodium nitrite, cuprous chloride, copper bronze and hydrochloric acid under conditions analogous to those of Example 1(e) gave 5-chloro-2-(4-aminobutyl)-3-methylpyridine (1.0 g) m.p. 118°–120° C.

(b) Reaction of 5-chloro-2-(4-aminobutyl)-3-methylpyridine [from Example 5(a)] (1.0 g) with 2-nitroamino-5-(6-methylpyrid-3-ylmethyl)-4-pyrimidone (1.23 g) under conditions analogous to those described in Example 1(f) gave 2-[4-(5-chloro-3-methylpyrid-2-yl)butylamino]-5-(6-methylpyrid-3-ylmethyl)-4-pyrimidone (0.53 g) m.p. 140°–141° C.

$C_{21}H_{24}ClN_5O$: Requires: C, 63.39; H, 6.08; N, 17.60; Cl, 8.91; Found: C, 63.18; H, 6.22; N, 17.42; Cl, 9.18.

Example 6

(a) 5-Nitro-3-methyl-2-cyanopropylpyridine (2 g) in tetrahydrofuran (20 ml) was reduced with diborane (0.045 mole) in tetrahydrofuran (45 ml) over 2 hours 20 minutes. The reaction mixture was added slowly to ethanol (100 ml), stirred for 1 hour, acidified with hydrochloric acid (100 ml, molar), stirred for 20 minutes and concentrated to low volume. The solution was washed with chloroform, basified with sodium hydroxide to pH 12 and extracted with chloroform to give 3-methyl-5-nitro-2-(4-aminobutyl)pyridine, as an oil (0.9 g) N.M.R. (CDCl$_3$) assignment, $\delta$(p.p.m.), multiplicity; (CH$_2$)$_2$CH$_2$NH$_2$, 1.4–1.9, m; NH$_2$, 1.98, broad s; 3—CH$_3$ 2.48, s, CH$_2$(CH$_2$)$_2$CH$_2$NH$_2$, 2.7–3.1, m; 4—H pyridyl, 8.21, d; 6—H pyridyl, 9.19, d.

(b) The product from Example 6(a) (0.85 g) was heated under reflux in pyridine (5 ml) with 2-nitroamino-5-(6-methylpyrid-3-ylmethyl)-4-pyrimidone (1.25 g) under nitrogen, for 6 hours. The pyridine was removed in vacuo and the residue was chromatographed on silica in chloroform-methanol to give 2-[4-(5-nitro-3-methylpyrid-2-yl)butylamino]-5-(6-methyl-pyrid-3-ylmethyl)-4-pyrimidone (0.345 g) m.p. 141°–142° C.

C$_{21}$H$_{24}$N$_6$O$_3$: Requires: C, 61.75; H, 5.92; N, 20.58; Found: C, 61.20; H, 5.92; N, 20.48.

Example 7

(a) 5-Amino-2-[4-aminobutyl]-3-methylpyridine (2.17 g) in 20% sulphuric acid (25 ml) at $-5°$ C. was reacted with a solution of sodium nitrite (1 g) in water (5 ml) over 20 minutes. After a further 15 minutes at $-9°$ C. the reaction mixture was added to a mixture of potassium iodide (4 g) and cuprous iodide (0.5 g) in water (65 ml) at 10° C. and then stirred at room temperature for 30 minutes. Saturated sodium thiosulphate solution (10 ml) was added and the pH was brought to 12 with sodium hydroxide. Chloroform extraction of the reaction mixture gave 5-iodo-3-methyl-2-(4-aminobutyl)pyridine as a dark oil (2.45 g). N.M.R. (CDCl$_3$) assignment, $\delta$ (p.p.m.), multiplicity; (CH$_2$)$_2$CH$_2$NH$_2$, 1.4–2.0, m; NH$_2$, 1.69, s; 3—CH$_3$, 2.28, s; CH$_2$(CH$_2$)$_2$CH$_2$NH$_2$, 2.76, m; 4—H pyridyl, 7.75, m; 6—H pyridyl, 8.57, m.

(b) The product of Example 7(a) (0.6 g) and 2-nitroamino-5-(6-methylpyrid-3-ylmethyl)-4-pyrimidone (0.6 g) were heated in pyridine (3 ml) for 5 hours. After removal of the pyridine in vacuo the residue was chromatographed in chloroform-methanol on silica to give 2-[4-(5-iodo-3-methylpyrid-2-yl)butylamino]-5-(6-methylpyrid-3-ylmethyl)-4-pyrimidone m.p. 160°–161.5° C.

Example 8

(a) A cooled (0° C.) mixture of 5-amino-2-[4-aminobutyl]-3-methylpyridine (0.86 g) and fluoroboric acid (5 ml) in ethanol (30 ml) was reacted with amyl nitrite (3 ml) over 15 minutes and then stirred for a further 15 minutes, diluted with diethyl ether at 0° C. to give 5-diazo-2-(4-aminobutyl)-3-methylpyridine fluoroborate (1.88 g) m.p. 80°–120° C. (dec.).

This salt (1.78 g) was added portionwise to petroleum ether (75 ml) stirred at 95°–100° C. to give an oil which solidified on cooling. The petroleum ether was decanted and the solid was partitioned between water and chloroform. The pH of the aqueous portion was raised to 13 with sodium hydroxide and the product was extracted with chloroform to give 5-fluoro-2-(4-aminobutyl)-3-methylpyridine (0.69 g) as an amber oil.

N.M.R. (CDCl$_3$) assignment $\delta$ (p.p.m.) multiplicity; NH$_2$, 1.39, broad s; CH$_2$CH$_2$CH$_2$CH$_2$NH$_2$, 1.4–1.9, m; 3—CH$_3$, 2.3, s; CH$_2$(CH$_2$)CH$_2$NH$_2$, 2.6–2.8, m; 4—H pyridyl, 7.14, d of d; 6—H pyridyl, 8.19, d;

(b) The product from Example 8(a) (0.60 g) was refluxed in pyridine (3 ml) with 2-nitroamino-5-(6-methyl-pyrid-3-yl-methyl)-4-pyrimidone (0.86 g) for 7 hours to give, after concentration, chromatography in chloroformmethanol, and crystallisation from acetonitrile, 2-[4-(5-fluoro-3-methylpyridyl-2-yl)butylamino]-5-(6-methyl pyrid-3-ylmethyl)-4-pyrimidone, (1.04 g) m.p. 131.5°–133.5° C.

C$_{21}$H$_{24}$FN$_5$O: Requires: C, 66.16; H, 6.35; N, 18.37; Found: C, 66.25; H, 6.36; N, 18.13.

Example 9

The product from Example 1(e) (2.1 gm) and 2-nitroamino-5-(5,6-dimethyl-N-oxo-pyrid-3-ylmethyl)-4-pyrimidone (2.51 gm) were refluxed in pyridine (6 ml) for 13.5 hrs. The pyridine was removed in vacuo, and the last traces of pyridine were removed by azeotroping with n-propanol. The residue was then dissolved in hot ethanol (50 ml) and any undissolved solid filtered off. The filtrate was concentrated while hot to 20 ml volume and on cooling white crystals deposited. These were recrystallised from ethanol and dimethylformamide to give 2-[4-(5-bromo-3-methylpyrid-2-yl)butylamino]-5-(5,6-dimethylpyrid-N-oxo-3-ylmethyl)-4-pyrimidone (2.5 gm) m.p. 204°–206° C.

C$_{22}$H$_{26}$BrN$_5$O$_2$: Requires: C, 55.81; H, 5.60; N, 15.00; Br, 17.23; Found: C, 55.93; H, 5.54; N, 14.82; Br, 16.92.

Example 10

The product from Example 1(e) (1.06 gm) and 2-nitroamino-5-(N-oxo-pyrid-4-ylmethyl)-4-pyrimidone (1.14 gm) were refluxed in anisole (4 ml) for 7.5 hrs. The anisole was removed in vacuo. The residue obtained was chromatographed on silica in chloroform-methanol (4:1). The product was crystallised from acetonitrile-water (9:1) to give 2-[4-(5-bromo-3-methylpyridyl-2-yl)-butylamino]-5-(N-oxo-pyrid-4-ylmethyl)-4-pyrimidone (0.40 gm) m.p. 110°–115° C.

C$_{20}$H$_{22}$BrN$_5$O$_2$: Requires: C, 54.06; H, 4.99; N, 15.76; Br, 17.98. C$_{20}$H$_{22}$BrN$_5$O$_2$.0.62H$_2$O Requires: C, 52.70; H, 5.14; N, 15.37; Br, 17.54; Found: C, 52.68; H, 4.92; N, 15.45; Br, 18.26.

Example 11

A mixture of 5-bromo-2-(4-aminobutyl)-3-methyl pyridine, (0.68 g) and 2-nitroamino-5-(4,6-dimethyl-3-pyridylmethyl)-4-pyrimidone (0.83 g) in anisole (25 ml) were refluxed for 4 hrs. Petroleum ether was added to precipitate the product which was then chromatographed on a silica gel column eluting with chloroform. The product was crystallised from ethyl acetate to give 2-[4-(5-bromo-3-methylpyrid-2-yl)-butylamino]-5-(4,6-dimethyl-3-pyridylmethyl)-4-pyrimidone (0.77 g) m.p. 110°–112° C.

C$_{22}$H$_{26}$N$_5$BrO, 1.27H$_2$O: Requires: C, 55.00; H, 6.01; N, 14.58; Br, 16.63; Found: C, 54.87; H, 5.93; N, 14.38; Br, 16.33; (Wt loss 40°–110° C.=1.33 H$_2$O).

Example 12

A mixture of 5-bromo-2-(4-aminobutyl)-3-methyl pyridine, (0.68 g) and 2-nitroamino-5-(5,6-dimethyl-3-pyridylmethyl)-4-pyrimidone (0.83 g) in anisole (25 ml) were refluxed for 4 hrs. Excess petroleum ether was added to precipitate the product which was then chromatographed on a silica gel column in CHCl₃. The product crystallised under ether to give 2-[4-(5-bromo-3-methyl-pyrid-2-yl)-butylamino]-5-(5,6-dimethyl-3-pyridylmethyl)-4-pyrimidone (0.6 g) m.p. 126°14 8° C.

$C_{22}H_{26}N_5BrO.0.6H_2O$: Requires: C, 56.45; H, 5.87; N, 14.96; Br, 17.07; Found: C, 56.44; H, 5.68; N, 14.82; Br, 16.96.

Example 13

Trifluoroacetic anhydride (1.9 ml) was mixed with a suspension of the product from Example 8 (1.6 gm), in dry dichloromethane (10 ml) and the mixture was allowed to stand for two days. The solvent was removed in vacuo, and the residue was dissolved in chloroform. The chloroform solution was washed with 10% sodium bicarbonate solution. Evaporation of the chloroform gave a solid (1.7 gm) which was crystallised from ethanol (10 ml) and adding water (20 ml). Solid obtained was recrystallised from acetonitrile-water (9:1) to give 2-[4-(5-bromo-3-methylpyrid-2-yl)-butylamino-]-5-(5-methyl-6-hydroxymethylpyrid-3-ylmethyl)-4-pyrimidone (0.99 gm) m.p. 136°–141° C.

$C_{22}H_{26}BrN_5O_2$: Requires: C, 55.93; H, 5.54; N, 14.82; Br, 16.92. $C_{22}H_{26}BrN_5O_2.2.0.H_2O$: Requires: C, 51.97; H, 5.95; N, 13.78; Br, 15.72; Found: C, 51.82; H, 5.89; N, 13.83; Br, 15.48.

Example 14

A solution of 1,2-ethanedisulphonic acid (15.3 g) in methanol (48 ml) was added to a solution of 2-[4-(5-bromo-3-methylpyrid-2-yl)-butylamino]-5-(6-methyl-pyrid-3-yl-methyl)-4-pyrimidone (20 g) in methanol (68 ml). A solid crystallised on cooling which was removed by filtration, washed with cold methanol and dried to yield the neutral ethanesulphonate salt of 2-[4-(5-bromo-3-methylpyrid-2-yl)-butylamino]-5-(6-methyl-pyrid-3-yl-methyl)-4-pyrimidone (31 g) m.p. 182°–5° C.

$C_{21}H_{24}N_5OBr.1.5C_2H_6O_6S_2.2H_2O$: Requires: C, 37.75; H, 4.88; N, 9.17; S, 12.60; Br, 10.46; Found: C, 37.60; H, 4.78; N, 9.10; S, 12.30; Br, 10.71.

Example 15

A pharmaceutical composition for oral administration is prepared containing

|   |   | % by weight |
|---|---|---|
| A | 2-[4-(5-bromo-3-methylpyrid-2-yl)-butylamino]-5-(6-methylpyrid-3-yl-methyl)-4-pyrimidone | 55 |
|   | Dibasic calcium phosphate dihydrate | 20 |
|   | Approved coloring agent | 0.5 |
|   | Polyvinylpyrrolidone | 4.0 |
|   | Microcrystalline Cellulose | 8.0 |
| B | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

Example 16

A pharmaceutical composition for injectable administration is prepared by forming a solution of 2-[4-(5-bromo-3-methyl-pyrid-2-yl)-butylamino]-5-(6-methyl-pyrid-3-ylmethyl)-4-pyrimidone hydrochloride salt in sterile water to give a 1 to 5% w/w solution. The solution is clarified by filtration and filled into vials which are sealed and sterilised. A suitable vial contains 2 ml of the solution.

I claim:

1. A compound of formula (2):

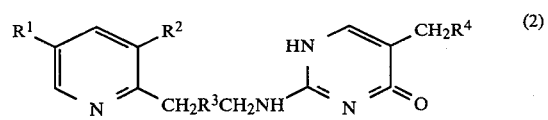

or a pharmaceutically acceptable salt thereof; where $R^1$ is halogen or nitro; $R^2$ is $C_{1-4}$ alkyl; $R^3$ is a $C_{1-3}$ alkylene group; and $R^4$ is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

2. A compound according to claim 1, where $R^1$ is bromine.

3. A compound according to claim 1 or claim 2, where $R^2$ is methyl.

4. A compound according to claim 1 or claim 2, where $R^4$ is pyrid-3-yl, 6-methyl-pyrid-3-yl, 6-hydroxymethyl-pyrid-3-yl or 5,6-dimethyl-6-pyrid-3-yl.

5. A compound according to claim 1 which is 2-[4-(5-bromo-3-methylpyrid-2-yl)butylamino]-5-(6-methylpyrid-3-ylmethyl)-4-pyrimidone or a pharmaceutically acceptable salt thereof.

6. A compound according to claim 1 which is 2-[4-(5-bromo-3-methylpyrid-2-yl)butylamino]-5-(pyrid-4-ylmethyl)-4-pyrimidone or a pharmaceutically acceptable salt thereof.

7. A compound according to claim 1 which is 2-[4-(5-bromo-3-methyl-pyrid-2-yl)butylamino]-5-(6-hydroxymethylpyrid-3-ylmethyl)-4-pyrimidone or a pharmaceutically acceptable salt thereof.

8. A hydrochloride salt of a compound of formula (2) according to claim 1.

9. A pharmaceutical composition having histamine $H_1$-antagonist activity comprising an effective amount of a compound according to claim 1 and a pharmaceutically acceptable carrier.

10. A method of blocking histamine $H_1$-receptors which comprises administering to a subject an effective amount to block said receptors of a compound according to claim 1.

11. A compound according to claim 5 which is 2-[4-(5-bromo-3-methylpyrid-2-yl)butylamino]-5-(6-methyl-pyrid-3-ylmethyl)-4-pyrimidone hydrochloride.

12. A compound according to claim 5 which is the neutral ethanesulphonate salt of 2-[4-(5-bromo-3-methylpyrid-2-yl)butylamino]-5-(6-methylpyrid-3-ylmethyl)-4-pyrimidone.

* * * * *